United States Patent
Virtanen

[19]
[11] Patent Number: 6,095,136
[45] Date of Patent: Aug. 1, 2000

[54] INHALATION DEVICE

[75] Inventor: Risto Virtanen, Nurmijärvi, Finland

[73] Assignee: Astra Aktiebolag, Sodertalje, Sweden

[21] Appl. No.: 09/066,368

[22] PCT Filed: Mar. 13, 1998

[86] PCT No.: PCT/SE98/00461

§ 371 Date: May 8, 1998

§ 102(e) Date: May 8, 1998

[87] PCT Pub. No.: WO98/41260

PCT Pub. Date: Sep. 24, 1998

[30] Foreign Application Priority Data

Mar. 14, 1997 [FI] Finland ................................. 9700943

[51] Int. Cl.$^7$ ................................................. A61M 15/00
[52] U.S. Cl. ............................ 128/203.15; 128/203.12; 128/200.18; 128/202.27
[58] Field of Search ..................... 128/203.15, 203.12, 128/203.21, 203.23, 203.24, 202.16, 202.17, 200.21, 200.24, 200.18, 202.27; 220/787, 23.87, 270, 917; 604/58

[56] References Cited

U.S. PATENT DOCUMENTS

| | | | |
|---|---|---|---|
| 1,680,882 | 8/1928 | Hollen | 220/23.87 |
| 2,579,280 | 12/1951 | Trumbour et al. | 604/58 |
| 2,604,094 | 7/1952 | Miller et al. | 128/203.15 |
| 2,641,254 | 6/1953 | Brown | 128/203.23 |
| 3,169,525 | 2/1965 | Bowen | 128/200.23 |
| 3,376,996 | 4/1968 | Bardell | 220/270 |
| 5,351,683 | 10/1994 | Chiesi et al. | 128/203.12 |
| 5,829,434 | 11/1998 | Ambrosi et al. | 128/203.15 |

FOREIGN PATENT DOCUMENTS

| | | |
|---|---|---|
| 0 237 507 | 9/1987 | European Pat. Off. . |
| 0 237 507 A1 | 9/1987 | European Pat. Off. . |
| 0 520 440 A1 | 12/1992 | European Pat. Off. . |
| WO95/32752 | 12/1995 | WIPO . |
| WO96/16687 | 6/1996 | WIPO . |

OTHER PUBLICATIONS

International Search Report.

*Primary Examiner*—John G. Weiss
*Assistant Examiner*—V. Srivastava
*Attorney, Agent, or Firm*—Fish & Richardson P.C.

[57] ABSTRACT

An inhaler for administering powder by inhalation and a method of constructing the same, the inhaler including a member which defines a chamber for containing desiccant, the member including first and second parts which when fitted together define the chamber for containing desiccant and include cooperating detent means for holding the same together on fitting, wherein the first part has an outer surface provided with at least one of an internal or external spline and the second part has an inner surface provided with at least one of the other of an internal or external spline, the splines being dimensioned and spaced relative to the cooperating detent means such that, when the first and second parts are fitted together, the at least one external spline is engaged within the at least one internal spline before any resistance to further insertion is caused by the cooperating detent means.

33 Claims, 3 Drawing Sheets

INHALATION DEVICE

BACKGROUND

The present invention relates to a powder inhaler and a method of constructing the same.

A number of powder inhalers are known which use different systems for introducing a dose of powder into an air stream. Typically, the powder is inhaled into the lungs of a patient in order to treat, for example, asthma.

One such powder inhaler is disclosed in EP-A-0237507. This inhaler comprises an inhalation channel and a mouthpiece comprising an air chamber and an outlet nozzle, which together define a flow path through which a stream of air is drawn during inhalation by a user. This inhaler further comprises means for introducing powder into the inhalation channel. During inhalation, air is first drawn into and through the inhalation channel so as to pick up powder. The stream of air containing powder is then drawn through the air chamber and out of the outlet nozzle of the mouthpiece.

Powder inhalers are, however, particularly susceptible to the effects of moisture and should therefore include a desiccant, such as silica gel, to absorb any moisture. It will of course be appreciated that it is a requirement that the desiccant be contained entirely separate from the powder to be inhaled so as to avoid contamination of the powder.

In powder inhalers of the kind which comprise an inhaler body and a grip portion at one end thereof, which grip portion is rotatable relative to the inhaler body so as to provide a dose of powder for inhalation, it has been proposed to provide a chamber in the grip portion for containing desiccant. In one proposed construction the grip portion comprises first and second parts which fit together to define a chamber; the first and second parts having cooperating splines to lock the same in the rotational sense and a cooperating circumferential groove and ridge to lock the same axially.

Normally, powder inhalers are assembled automatically by machine. However, automatic assembly would be problematic where the grip portion comprises first and second parts which have to be fitted together. This problem would arise particularly because of the fact that the parts would have to be pressed together with a significant force sufficient at least to engage the ridge and the groove, and, if, as is likely, the parts are not first precisely aligned, both rotationally and axially, the parts could be forced together at an angle such that the splines are damaged and/or the grip portion is not assembled correctly.

It is an aim of the present invention to provide a powder inhaler which includes a chamber for containing desiccant that can be formed simply and reliably.

SUMMARY OF THE INVENTION

Accordingly, the present invention provides an inhaler for administering powder by inhalation which comprises a member that defines a chamber for containing desiccant, the member comprising first and second parts which when fitted together define the chamber for containing desiccant and comprise cooperating detent means for holding the same together on fitting, wherein the first part has an outer surface provided with at least one of an internal or external spline and the second part has an inner surface provided with at least one of the other of an internal or external spline, the splines being dimensioned and spaced relative to the cooperating detent means such that, when the first and second parts are fitted together, the at least one external spline is engaged within the at least one internal spline before any resistance to further insertion is caused by the cooperating detent means.

Preferably, the splines are configured such that the axes of the first and second parts are substantially relatively angularly immovable before any resistance to further insertion is caused by the cooperating detent means.

Preferably, the relative lengths and positions of the splines are such that at least one-third of the length of each of the external and internal splines is engaged before any resistance to further insertion is caused by the cooperating detent means.

Preferably, the at least one internal spline extends from a position sufficiently near to the peripheral edge of the surface in which the same is provided that, on fitting together the first and second parts, the splines engage before any resistance to further insertion is caused by the cooperating detent means.

Preferably, the cooperating detent means comprise an at least part circumferential groove and an at least part circumferential ridge which is configured to engage therewithin.

More preferably, the at least part circumferential ridge is provided on the outer surface of the first part and the at least part circumferential groove is provided in the inner surface of the second part.

Still more preferably, the at least part circumferential groove is provided in the inner surface of the second part between the peripheral edge of the inner surface and the at least one spline provided to the inner surface.

Preferably, the at least one external spline is about three-quarters of the length of the at least one internal spline.

Preferably, the outer surface of the first part is provided with at least one external spline and the inner surface of the second part is provided with at least one internal spline.

Preferably, the inhaler further comprises an inhaler body and a mouthpiece from which powder is in use inhaled, the inhaler body housing a dosing mechanism for providing a dose of powder for inhalation.

More preferably, the member comprises a grip portion for operating the dosing mechanism.

Still more preferably, the grip portion is rotatably mounted to the inhaler body.

Yet still more preferably, the inhaler body comprises one of an at least part circumferential ridge or an at least part circumferential groove and the grip portion comprises the other of the at least part circumferential ridge or at least part circumferential groove, the at least part circumferential ridge being configured to engage within the at least part circumferential groove.

Preferably, at least a part of a wall of the chamber adjacent the inhaler body is permeable to moisture.

Preferably, the outer surface of the second part has a knurled or ridged surface which can be gripped by a user.

Preferably, the one of the first and second parts which is provided with the at least one internal spline includes at least one element which is disposed so as to be abutted by at least one of the at least one external spline when the first and second parts are fitted together.

Preferably, at least one of the at least one internal spline is bridged at the forward end in the direction of fitting by an element at least one of which is abutted by the at least one external spline when the first and second parts are fitted together.

More preferably, each element is formed of a material which is deformed by the respective external spline.

The present invention also provides a method of constructing an inhaler for administering powder by inhalation which comprises a member that defines a chamber for containing desiccant, the method comprising the steps of: providing first and second parts having respectively an outer surface and an inner surface, which when fitted together define the chamber for containing desiccant; providing the first and second parts with cooperating detent means for holding the same together on fitting; providing the outer surface of the first part with at least one of an internal or external spline and the inner surface of the second part with at least one of the other of an internal or external spline, the splines being dimensioned and spaced relative to the cooperating detent means such that, when the first and second parts are fitted together, the at least one external spline is engaged within the at least one internal spline before any resistance to further insertion is caused by the cooperating detent means; and fitting the first and second parts together to define the chamber for containing desiccant.

In this way, the first and second parts may be put together with the internal and external splines interlocking before any significant force need be applied. With the splines interlocking, and, therefore, the first and second parts aligned, a force may then be applied to engage the detent means and hence axially fix the first and second parts without damaging the splines. With the splines engaging, the first and second parts are disposed with the axes thereof parallel, such that, when the first and second parts are driven together, the first and second parts move squarely and the bottom peripheral edge of the first part cannot be driven into the side of the second part.

In the inhaler of the present invention the chamber is formed easily by merely pressing together the first and second parts. In particular, the construction of the inhaler of the present invention ensures that the significant force required to clip the first and second parts together need not be applied until the first and second parts are aligned and significantly engaged. In other words, during assembly, the first and second parts would not be forced together in a misaligned state.

Preferred embodiments of the present invention will now be described hereinbelow by way of example only with reference to the accompanying drawings.

DETAILED DESCRIPTION OF THE PREFERRED EMBODIMENTS

Figure 1:
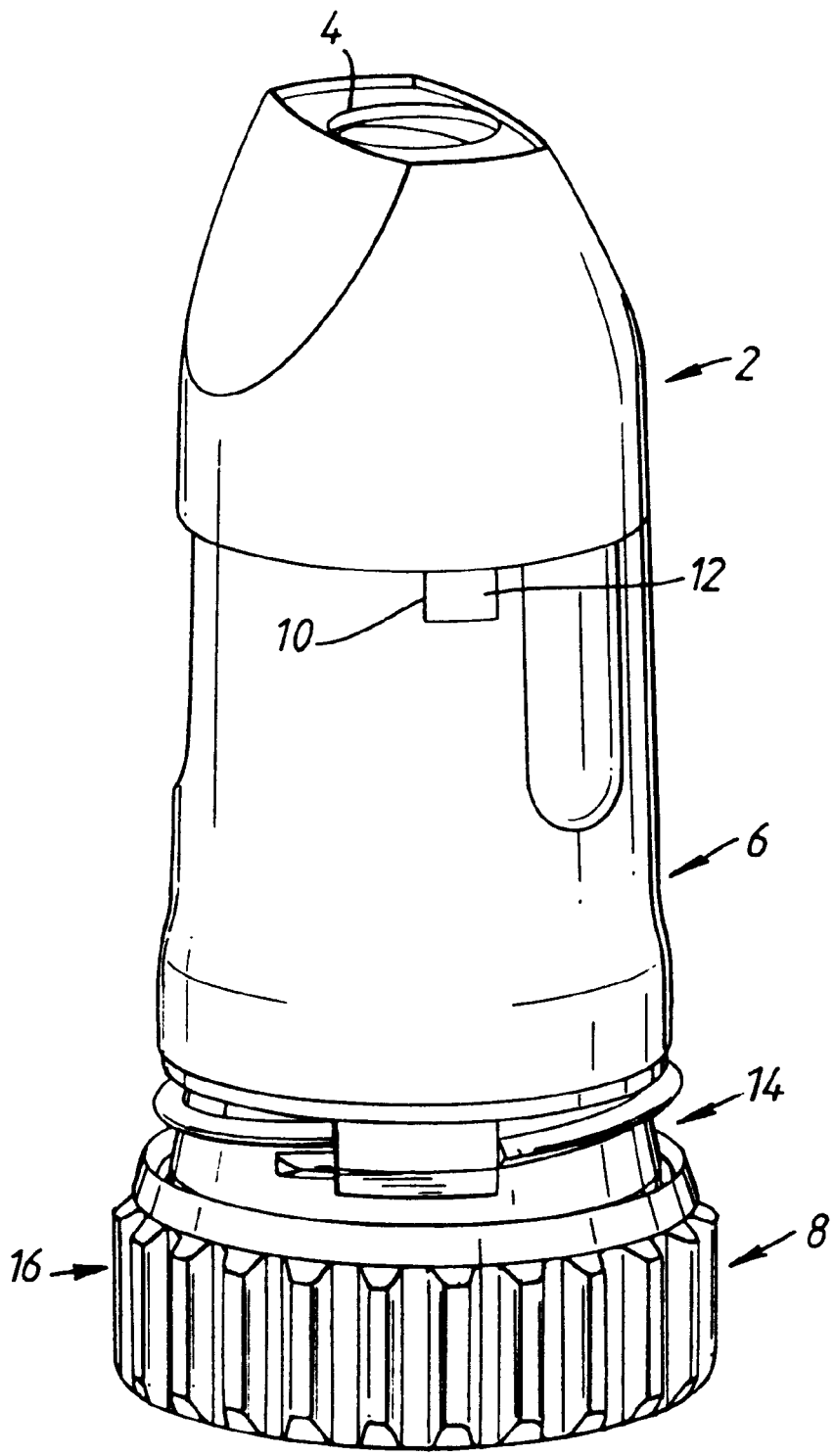
FIG. 1 illustrates a perspective view of a powder inhaler in accordance with a first embodiment of the present invention.
Figure 2:
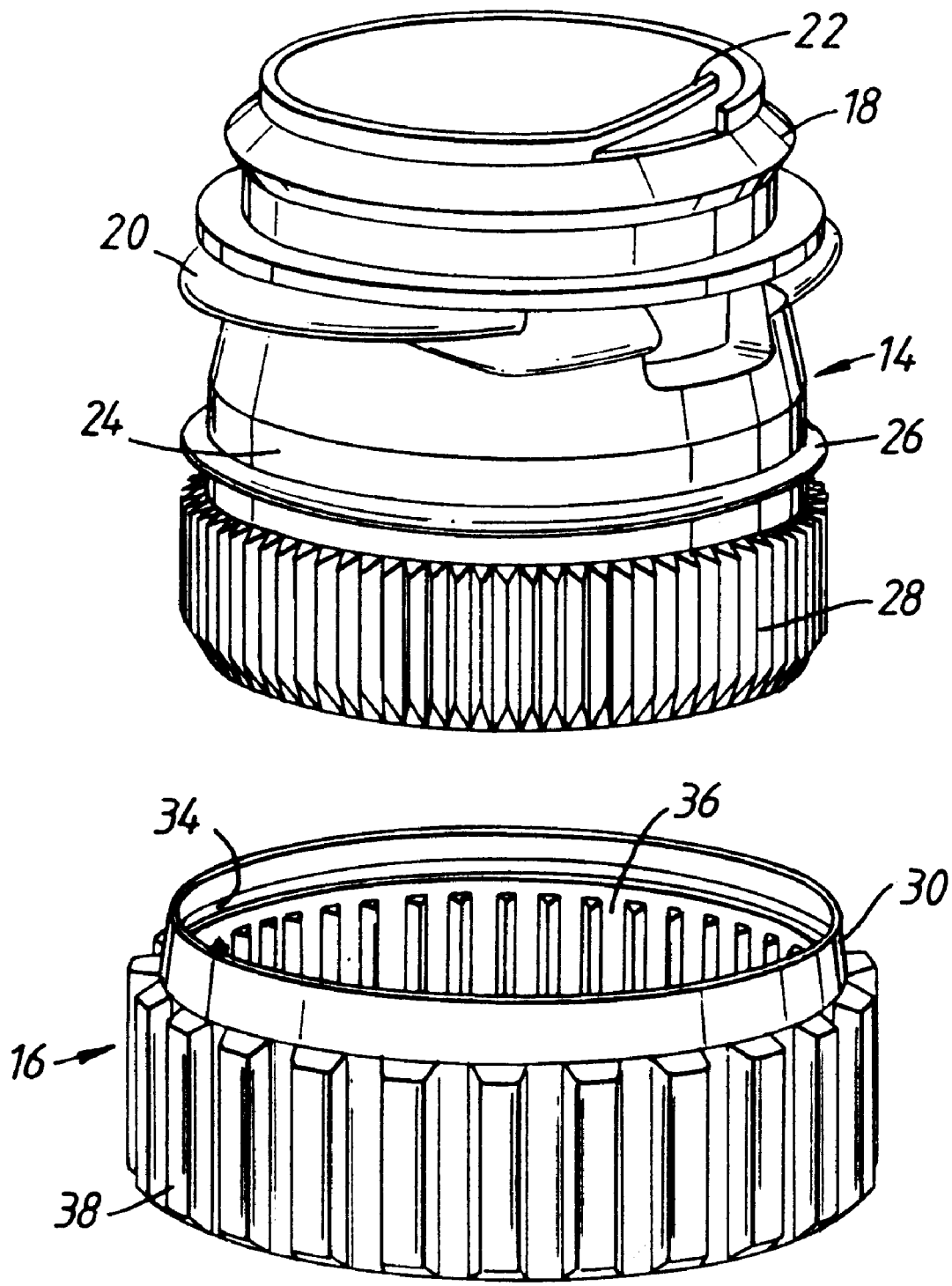
FIG. 2 illustrates in exploded view the component parts of the grip portion of the inhaler of FIG. 1.

FIG. 1 illustrates a powder inhaler in accordance with a first embodiment of the present invention. The inhaler comprises a mouthpiece 2 comprising an outlet nozzle 4, an inhaler body 6 and a rotatable grip portion 8 for operating a dosing mechanism disposed in the inhaler body 6 for providing doses of powder for inhalation. The inhaler body 6 is provided with an opening 10 which is filled with a window 12 through which an indicating wheel (not illustrated) is visible so as to provide an indication as to the usage of the inhaler.

In use, the grip portion 8 is first rotated in one sense, this embodiment in the counterclockwise sense when viewed from above, through a predetermined angle relative to the inhaler body 6 and then rotated in the opposite, clockwise, sense back to the original position. This action operates the dosing mechanism to provide a dose of powder for inhalation. The user then takes the mouthpiece 2 in the lips and inhales so as to draw powder into the lungs.

The grip portion 8 comprises first and second hollow parts 14, 16 which are mutually configured so as to define an enclosed chamber (not illustrated) for containing desiccant when fitted together.

The first part 14 comprises a circumferential ridge 18 disposed about the outer surface of one, the upper, end thereof to which the inhaler body 6 is clipped and external threads 20 to which a cap (not illustrated) having corresponding internal threads is screwed so as to cover the mouthpiece 2 and the inhaler body 6 and thus form a tight seal. The first part 14 further comprises an upwardly-directed resiliently-biased arm 22 disposed at the periphery of the upper end thereof, which arm 22, on rotation of the grip portion 8, engages part of the dosing mechanism so as to provide a dose of powder for inhalation. The first part 14 yet further comprises a tubular section 24, in this embodiment of generally cylindrical cross-section, one, the upper, end of which is closed by a wall (not illustrated) which is permeable to moisture. In a preferred embodiment the wall is formed of cardboard. The outer surface of the tubular section 24 includes a circumferential ridge 26 and a plurality of external splines 28, in this embodiment of triangular cross-section.

The second part 16 comprises a tubular section 30, in this embodiment of generally cylindrical cross-section, one, the lower, end of which is closed by a wall 32. The inner surface of the tubular section 30 includes a circumferential groove 34 at the upper end thereof and a plurality of internal splines 36, in this embodiment of quadrilateral cross-section with outwardly-flaring flanks. The outer surface of the tubular section 30 includes a plurality of axially-directed ridges 38 which are gripped by a user on rotation of the grip portion 8. In another embodiment the outer surface of the tubular section 30 could be knurled. In this embodiment the inner dimension of the tubular section 30 is configured so as to be a close radial fit over the tubular section 24 of the first part 14.

With this construction, the first and second parts 14, 16 are clipped together on locating the ridge 26 in the groove 34; relative rotation of the first and second parts 14, 16 being prevented by the mating splines 28, 36.

The splines 28, 36 are configured, in terms of axial position and axial length, so as to be substantially entirely interengaged before the upper end of the tubular section 30 meets the ridge 26. In practice, it is sufficient for the internal splines 36 to extend near to the upper end of the tubular section 30, though how near is dependent of course upon how near the external splines 28 extend to the lower end of the tubular section 24. If the external splines 28 are relatively long, the internal splines 36 may be relatively short, and, conversely, if the external splines 28 are relatively short, the internal splines 36 must be relatively long.

It will of course be appreciated that the splines 28, 36 can have any dimension and spacing which are such as to fix the first and second parts 14, 16 rotationally relative to one another. In a preferred embodiment, however, the splines 28, 36 are configured so as to fix the first and second parts 14, 16 rotationally relative to one another irrespective of the relative angular position of the first and second parts 14, 16 when fitted together.

In this embodiment the external splines 28 are spaced differently to the internal splines 36 such that when the first and second parts 14, 16 are fitted together axially-extending spaces exist between the splines 28, 36. In this way, if particles of desiccant happen to pass between the splines 28, 36 during assembly, those desiccant particles will not impede assembly, but rather fall into the spaces.

Figure 3:
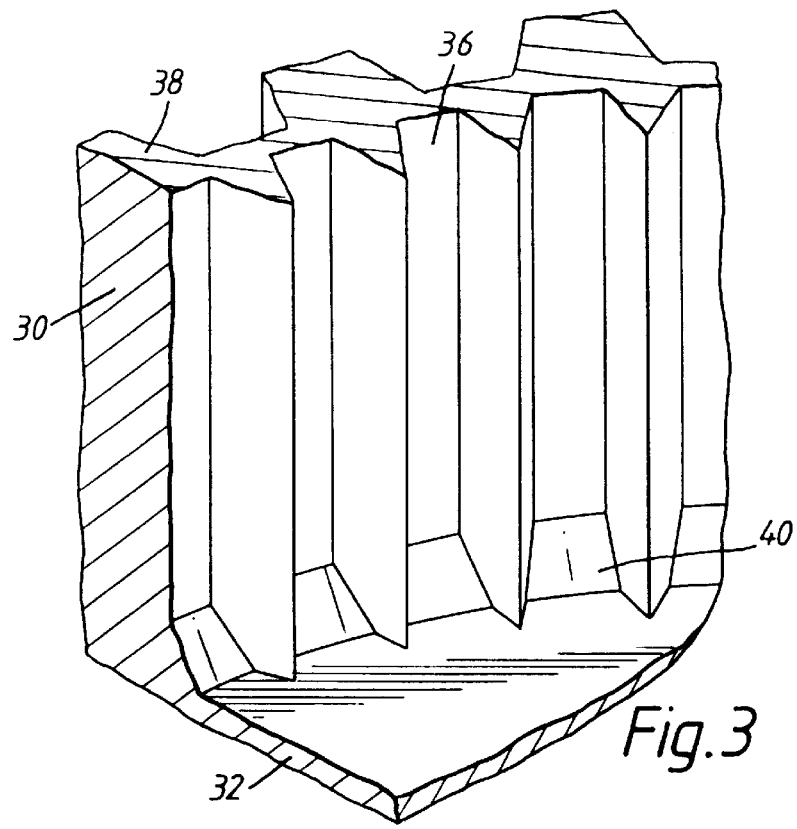
FIG. 3 illustrates a fragmentary part sectional view of the inner surface of one component part of the grip portion of the inhaler of FIG. 1.

As illustrated in FIG. 3, the ends of the internal splines 36 adjacent the end wall 32, in this embodiment at the junction between the tubular section 30 and the end wall 32, include elements 40 which bridge the flanks thereof In this embodiment the elements 40 are of triangular cross-section with the hypotenuse facing upwardly and inwardly relative to the inner surface of the tubular section 30. It is not necessary that all of the internal splines 36 be bridged by elements 40. However, for ease of moulding and optimum effect, the elements 40 are provided by a circumferential bead. The purpose of the elements 40 is as follows. When the external splines 28 are passed into the internal splines 36, the lower ends of the external splines 28 contact the respective elements 40 before the ridge 26 is located in the groove 34. In this way, when the ridge 26 is located in the groove 34 and the first and second parts 14, 16 are fitted together, the external splines 28 cut into the respective elements 40 so as further to anchor the first and second parts 14, 16 together, both in a rotational and an axial sense.

Figure 4:
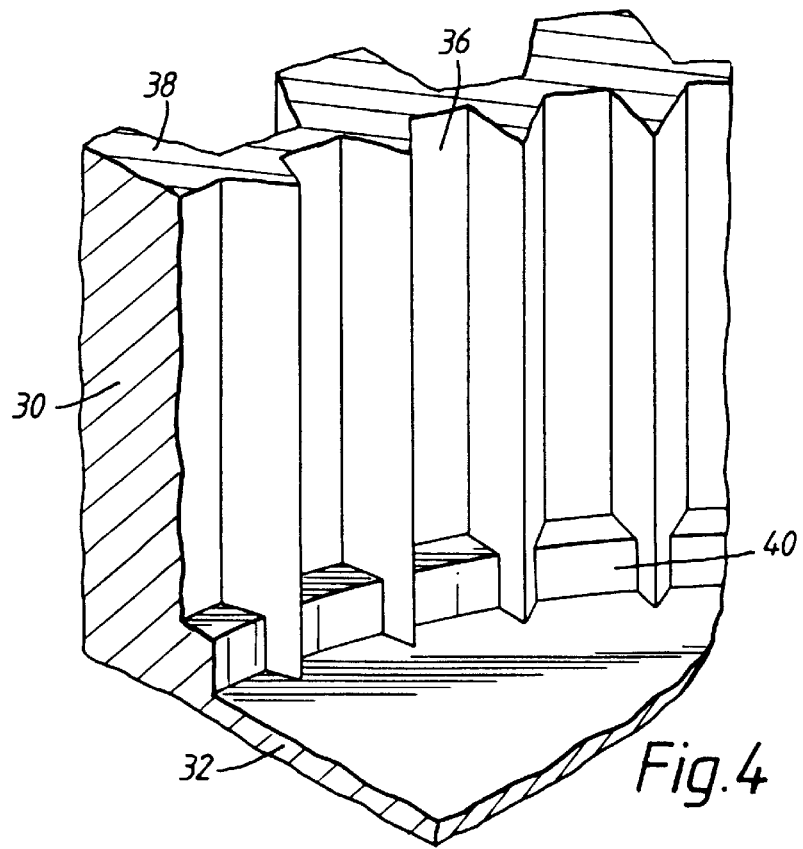
FIG. 4 illustrates a fragmentary part sectional view of the inner surface of one component part of the grip portion of an inhaler in accordance with a second embodiment of the present invention.

FIG. 4 illustrates the inner surface of the second part 16 of the grip portion 8 of an inhaler in accordance with a second embodiment of the present invention. The inhaler of this embodiment is almost identical in structure to the inhaler of the above-described first embodiment and differs only in that the elements 40 bridging the internal splines 36 are of square cross-section, with one surface of the elements 40 being parallel to the inner surface of the tubular section 30.

Finally, it will be understood by a person skilled in the art that the present invention has been described in its preferred embodiments and can be modified in many different ways without departing from the scope of the invention as defined in the appended claims.

In another embodiment the circumferential ridge 26 could be disposed at the lower end of the tubular section 24, that is forward of the external splines 28 in the direction of fitting, and the circumferential groove 34 disposed at the lower end of the tubular section 30, that is forward of the internal splines 36 in the direction of fitting. Thus, in the same manner as the above-described embodiments, the ridge 26 will not engage in the groove 34 until after the splines 28, 36 are interlocked.

In yet another embodiment the circumferential ridge 26 could be replaced by a circumferential groove and the circumferential groove 34 replaced by a circumferential ridge.

In still yet another embodiment the first part 14 could be provided with internal splines and the second part 16 provided with external splines.

What is claimed is:

1. An inhaler for administering powder by inhalation which comprises a member that defines a chamber for containing desiccant, the member comprising first and second parts which when fitted together define the chamber for containing desiccant and comprise cooperating detent means for holding the first and second parts together on fitting, wherein the first part has an outer surface provided with at least one of an internal or external spline and the second part has an inner surface provided with at least one of the other of an internal or external spline, the splines being dimensioned and spaced relative to the cooperating detent means such that, when the first and second parts are fitted together, the at least one external spline is engaged within the at least one internal spline before any resistance to further insertion is caused by the cooperating detent means.

2. The inhaler according to claim 1, wherein the splines are configured such that the axes of the first and second parts are substantially relatively angularly immovable before any resistance to further insertion is caused by the cooperating detent means.

3. The inhaler according to claim 1, wherein the relative lengths and positions of the splines are such that at least one-third of the length of each of the external and internal splines is engaged before any resistance to further insertion is caused by the cooperating detent means.

4. The inhaler according to claim 1, wherein the at least one internal spline extends from a position sufficiently near to a peripheral edge of the surface in which the internal spline is provided that, on fitting together the first and second parts, the internal and external splines engage before any resistance to further insertion is caused by the cooperating detent means.

5. The inhaler according to claim 1, wherein the cooperating detent means comprise an at least part circumferential groove and an at least part circumferential ridge which are configured to engage each other.

6. The inhaler according to claim 5, wherein the at least part circumferential ridge is provided on the outer surface of the first part and the at least part circumferential groove is provided in the inner surface of the second part.

7. The inhaler according to claim 6, wherein the at least part circumferential groove is provided in the inner surface of the second part between a peripheral edge of the inner surface and the at least one spline provided to the inner surface.

8. The inhaler according to claim 1, wherein the at least one external spline is about three-quarters of the length of the at least one internal spline.

9. The inhaler according to claim 1, wherein the outer surface of the first part is provided with at least one external spline and the inner surface of the second part is provided with at least one internal spline.

10. The inhaler according to claim 1, further comprising an inhaler body and a mouthpiece from which powder is in use inhaled, the inhaler body housing a dosing mechanism for providing a dose of powder for inhalation.

11. The inhaler according to claim 10, wherein the member comprises a grip portion for operating the dosing mechanism.

12. The inhaler according to claim 11, wherein the grip portion is rotatably mounted to the inhaler body.

13. The inhaler according to claim 12, wherein the inhaler body comprises one of an at least part circumferential ridge or an at least part circumferential groove and the grip portion comprises the other of the at least part circumferential ridge or at least part circumferential groove, the at least part circumferential ridge being configured to engage within the at least part circumferential groove.

14. The inhaler according to claim 10, wherein at least a part of a wall of the chamber adjacent the inhaler body is permeable to moisture.

15. The inhaler according to claim 10, wherein the outer surface of the second part has a knurled or ridged surface which can be gripped by a user.

16. The inhaler according to claim 1, wherein the one of the first and second parts which is provided with the at least one internal spline includes at least one element which is disposed so as to be abutted by at least one of the at least one external spline when the first and second parts are fitted together.

17. The inhaler according to claim 1, wherein at least one of the at least one internal spline is bridged at a forward end in the direction of fitting by an element at least one of which is abutted by the at least one external spline when the first and second parts are fitted together.

18. The inhaler according to claim 16, wherein the element disposed to be abutted is formed of a material which is deformed by the respective external spline.

19. A method of constricting an inhaler for administering powder by inhalation which comprises a member that defines a chamber for containing desiccant, the method comprising the steps of:

providing a first part having an outer surface and a second part having an inner surface, which when fitted together define the chamber for containing desiccant;

providing the first and second parts with cooperating detent means for holding the first and second parts together on fitting;

providing the outer surface of the first part with at least one of an internal or external spline and the inner surface of the second part with at least one of the other of an internal or external spline, the splines being dimensioned and spaced relative to the cooperating detent means such that, when the first and second parts are fitted together, the at least one external spline is engaged within the at least one internal spline before any resistance to further insertion is caused by the cooperating detent means; and fitting the first and second parts together to define the chamber for containing desiccant.

20. A dry powder inhaler comprising an element which defines a chamber for containing desiccant, said element comprising:

a first part comprising a first detent structure and having an outer surface comprising a first spline; and a second part comprising a second detent structure sized and shaped to mate with the first detent structure and having an inner surface comprising a second spline sized and shaped to mate with the first spline, wherein, when said first part and said second part are fitted together to define the chamber for containing desiccant, the first and second splines engage each other before the first and second detent structures engage each other, holding said first part to said second part.

21. The inhaler of claim 20 wherein both said first part and said second part have a generally cylindrical shape, where the outer surface of said first part has a diameter less than or equal to a diameter of the inner surface of said second part, and said first and second parts, when fitted together, share a common central axis.

22. The inhaler of claim 21 wherein the first and second splines, when engaged with each other, prevent said first part from rotating relative to the said second part about the common central axis, and the first and second detent structures, when engaged with each other, prevent said first part from sliding relative to said second part in the direction of the common central axis.

23. The inhaler of claim 22 wherein the first detent structure comprises a groove, and the second detent structure comprises a ridge, where the groove and the ridge are sized and shaped to mate with each other.

24. The inhaler of claim 22, wherein the first detent structure comprises a ridge, and the second detent element comprises a groove, where the groove and the ridge are sized and shaped to mate with each other.

25. The inhaler of claim 20 wherein the first spline is an external spline having a generally triangular cross-section, and the second spline is internal spline having a generally quadrilateral cross-section.

26. The inhaler of claim 20 wherein the first spline is an internal spline having a generally quadrilateral cross-section, and the second spline is an external spline having a generally triangular cross-section.

27. The inhaler of claim 20 wherein one of said first spline or said second spline is an internal spline and the other spline is an external spline, where the internal spline comprises an abutting element which bridges the internal spline at a far end, such that when the external spline engages the internal spline, the external spline contacts the bridging element before the detent members fully engage.

28. The inhaler of claim 27 wherein the abutting element comprises a deformable material, such that the external spline cuts into the abutting element when said first part and said second part are fitted together, whereby the abutting element assists in holding said first part to said second part.

29. The inhaler of claim 20 wherein said first part comprises a plurality of first splines, and said second part comprises a plurality of second splines.

30. The inhaler of claim 20 wherein the inhaler further comprises a body and a mouthpiece, the inhaler body comprising a dosing mechanism for providing a dose of powder for inhalation.

31. The inhaler of claim 30 wherein said element defining the chamber further comprises an upper wall between said element defining the chamber and the housing of the inhaler, and a lower wall, where said first part, said second part, said upper wall, and said lower wall define and enclose the chamber.

32. The inhaler of claim 31 wherein said upper wall is permeable to moisture.

33. The inhaler of claim 32 wherein said upper wall is constructed from cardboard.

* * * * *